United States Patent [19]

Smith

[11] Patent Number: 5,426,980

[45] Date of Patent: Jun. 27, 1995

[54] BOOTED ULTRASONIC TRANSDUCER

[75] Inventor: Thurman D. Smith, San Jose, Calif.

[73] Assignee: General Electric Company, San Jose, Calif.

[21] Appl. No.: 92,860

[22] Filed: Jul. 19, 1993

[51] Int. Cl.$^6$ ............................................. G01N 29/28
[52] U.S. Cl. ........................................ 73/644; 73/632
[58] Field of Search ................. 73/644, 639, 596, 617, 73/627, 629, 632; 128/662.03

[56] References Cited

U.S. PATENT DOCUMENTS

| | | | |
|---|---|---|---|
| H1,290 | 2/1994 | Mann et al. | 73/644 |
| 2,532,507 | 12/1950 | Meunier | 73/600 |
| 2,592,134 | 4/1952 | Firestone | 73/629 |
| 2,660,054 | 11/1953 | Pringle, Jr. | 73/627 |
| 2,740,289 | 4/1956 | Van Valkenburg | 73/620 |
| 2,913,602 | 11/1959 | Joy | 73/644 |
| 3,175,106 | 3/1965 | Sansom et al. | 73/644 |
| 3,497,728 | 2/1970 | Ostrofsky et al. | 73/644 |
| 3,628,375 | 12/1971 | Pagano | 73/644 |
| 3,777,552 | 12/1973 | Fletcher et al. | 73/622 |
| 4,020,679 | 5/1977 | Barry | 73/644 |
| 4,603,701 | 8/1986 | Chen | 73/644 |
| 4,796,632 | 1/1989 | Boyd | 128/662.03 |
| 4,977,780 | 12/1990 | Machida | 73/644 |

FOREIGN PATENT DOCUMENTS

| | | | |
|---|---|---|---|
| 613239 | 11/1948 | United Kingdom . | |
| 664606 | 1/1952 | United Kingdom | 73/644 |
| 1670581 | 8/1991 | U.S.S.R. | 73/596 |

OTHER PUBLICATIONS

Drawing of Mark IV Oil-Filled Ultrasonic Search Unit, no date supplied.

Primary Examiner—Hezron E. Williams
Assistant Examiner—Christine K. Oda
Attorney, Agent, or Firm—James E. McGinness

[57] ABSTRACT

A soft membrane booted transducer for performing ultrasonic inspections of parts and components that have rough sound beam entry surfaces. These rough surfaces may be in the form of as-welded unprepared overlays, cladded components, as-cast parts, or other unprepared surfaces that tend to prohibit, or prevent, sound entry from normal, smooth, hard-surfaced transducer contacting shoes made from Lucite or similar materials. The booted ultrasonic transducer has a soft membrane boot for coupling the transducer to an uneven or rough sound beam entry surface. The soft membrane is made of a flexible material capable of transmitting ultrasonic waves. When pressed into contact with the uneven or rough surface of the object being inspected, the membrane flexes to generally conform to the shape of the contacted surface. Flexing of the membrane eliminates or reduces air gaps between the transducer and the object surface, thereby increasing the ultrasonic coupling between the piezoelectric element and the object.

6 Claims, 3 Drawing Sheets

BOOTED ULTRASONIC TRANSDUCER

FIELD OF THE INVENTION

This invention relates generally to non-destructive examination of material, such as metal or alloy, for voids, flaws, cracks and other defects that can be detrimental to the integrity of the material. Specifically, the invention relates to the ultrasonic inspection of parts and components that have rough sound beam entry surfaces.

BACKGROUND OF THE INVENTION

Ultrasonic examinations are performed within the nuclear industry and most other major industries to determine the condition of parts and components. The metal or alloy material of a part or component is inspected using ultrasound to detect any flaws which could prove detrimental to the safe operation of that part or component. The ultrasonic nondestructive examination method can be used to detect internal flaws in most engineering metals and alloys. Bonds produced by welding, brazing, soldering and adhesive bonding can also be ultrasonically inspected.

Ultrasonic inspection is used for quality control and materials inspection in the fabrication of structures, reactor pressure vessels, airframes, pipe systems, bridges, motor vehicles and jet engines. The present invention has application in all of these fields.

For successful application of ultrasonic examination techniques, methods and equipment, the ultrasonic system, including transducers, must be suitable for the type of inspection being performed. If the correct transducer is not used, there is a high potential for gross error in the inspection results, or there could be no results at all. For instance, using a common ultrasonic transducer that has a hard flat-surfaced LUCITE wedge for examining as-welded overlaid pipe welds results in gross errors in the ultrasonic inspection results. In many cases ultrasonic inspection data is not recorded at all. This is due to the presence of air gaps between the transducer head and the rough surface being inspected, which form an opaque barrier.

Ultrasonic characterization of cracks in materials is at least a two-step process: 1) detection and location; and 2) sizing in absolute or relative terms. In accordance with the first step of this process, the transducer is excited to emit a longitudinal ultrasonic wave which is coupled to the structure being inspected. The emitted wave enters the structure, where it is reflected by the crack. The return path of the reflected wave impinges on the transducer, where it is detected as a "pulse echo" signal.

The determination of the crack size, or depth of penetration in the case of surface-connected flaws, is a different and more complicated task. A conventional method for determining the depth of penetration of a planar crack is the time-of-flight diffraction technique. This method takes advantage of the forward scattering of waves of ultrasonic energy at the edges of a crack. An emitter of short pulses of ultrasound, coupled to the inspection surface, causes refracted sound waves to impinge on the crack edge, which scatters the ultrasonic energy in all directions. A detector situated on the opposite side of the crack plane is excited by the ray of scattered pulsed energy after a time delay that is a function of the crack height and other dimensions. By measuring the time-of-flight of the pulses from the emitter to the detector by way of the crack edge, the crack height can be easily computed from the geometry.

Inspection methods using the ultrasonic time-of-flight diffraction technique have been devised for buried, as well as surface-connected, cracks and have proven to be the most accurate means of crack sizing in practice. Corrections for surface curvature effects are employed for use with pipes and nozzles, where necessary, to enhance accuracy. On the other hand, the method clearly fails if the scattered wave is unable to reach the detector, which occurs if there is a relatively non-uniform gap interposed between the transducer and the surface being inspected. Such gaps arise when a hard, flat-surfaced ultrasonic transducer overlies an uneven or rough sound beam entry surface, such as a pipe weld in as-welded condition, i.e., without post-weld machining.

Booted transducers are known to have existed within the nondestructive examination industry in the past. One known design contains relatively small transducers installed within a large plastic case. The coupling medium used in that prior art booted transducer is a low-viscosity compressor oil. The angle of incidence for the ultrasonic wave produced by the transducers is determined by a holding bracket installed inside the plastic case on which the transducers are mounted. After installation of a holding bracket corresponding to the desired angle of incidence, the transducer is installed, the plastic boot is fixed in place and the whole assembly is filled with oil.

The foregoing type of booted transducer tends to be extremely large and its contact footprint often is too large for the part to be examined. Another limitation of this prior art assembly is that changing the transducer is difficult. First the oil must be drained; then the boot must be removed. If the angle of incidence is to be changed, the original holding bracket must be removed and another bracket corresponding to a different angle of incidence must be installed. The transducer is then installed and the whole assembly process is repeated. Very often the transducer assembly must be left idle while air bubbles rise to the surface of the oil and then are bled off. In general, this is an extremely time-consuming and inefficient process, especially when performed in hostile environments such as nuclear power plants.

SUMMARY OF THE INVENTION

The present invention is an improved booted ultrasonic transducers which is free of the shortcomings of the prior art booted transducer. The booted transducer of the invention alleviates the aforementioned contact problems which attend pipe welds that have been overlaid and left in the as-welded condition as well as other as-welded components with rough contact surfaces.

The apparatus of the invention is an ultrasonic transducer having a soft membrane boot for coupling the transducer to an uneven or rough sound beam entry surface. The soft membrane is made of a flexible material capable of transmitting ultrasonic waves. When pressed into contact with the uneven or rough surface of the object being inspected, the membrane flexes to generally conform to the shape of the contacted surface. Flexing of the membrane eliminates or reduces air gaps between the transducer and the object surface, thereby increasing the coupling of ultrasonic energy into and out of the object. The result is enhanced detection of cracks and other flaws in parts or components which have uneven or rough surfaces.

DETAILED DESCRIPTION OF THE PREFERRED EMBODIMENTS

Figure 1:
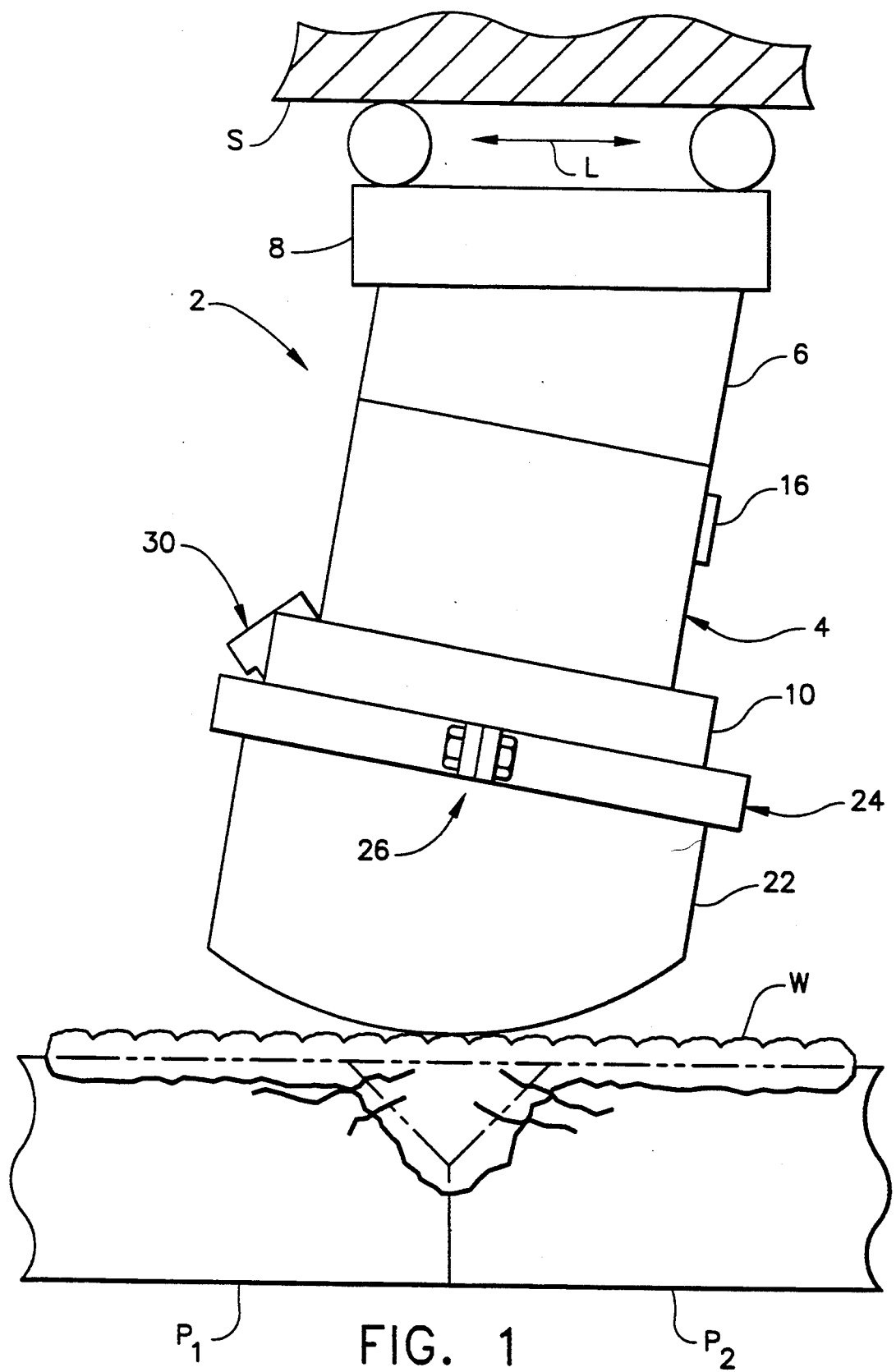
FIG. 1 is an assembly drawing of a booted ultrasonic transducer in accordance with a first preferred embodiment of the invention, the transducer being shown in contact with but not pressed against the surface of an object to be inspected.
Figure 2:
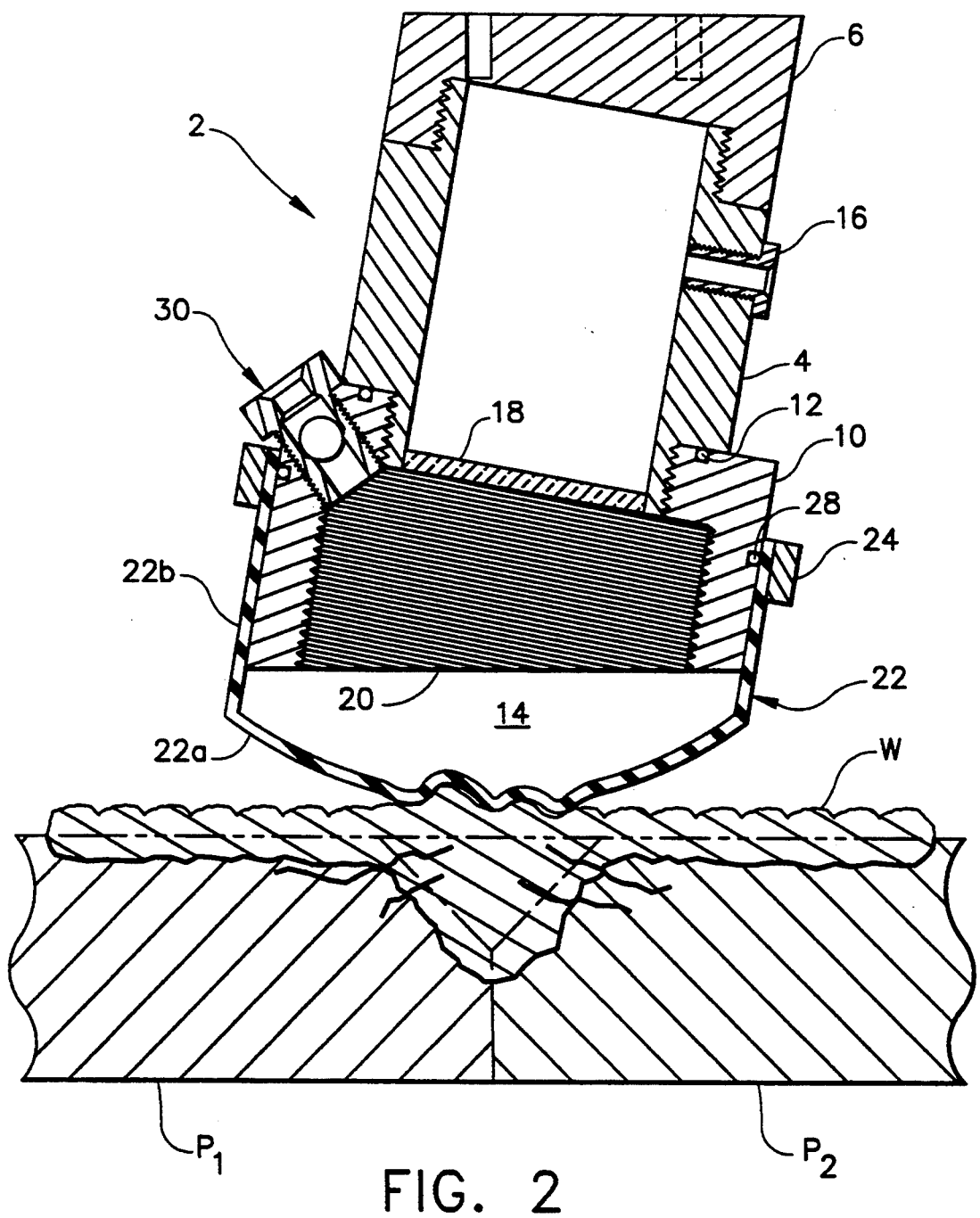
FIG. 2 is a sectional view of the booted transducer shown in FIG. 1, but with the transducer pressed against the object surface.

In accordance with a first preferred embodiment of the invention depicted in FIGS. 1 and 2, booted ultrasonic transducer 2 has an oversized transducer housing 4. The transducer housing 4 has a threaded radial bore for receiving a threaded connector 16, through which passes electrical wiring (not shown). A piezoelectric element 18 is fitted into the bottom of the transducer housing 4. The aforementioned electrical wiring is soldered to connect piezoelectric element 18 to pulser and receiver circuits (not shown). Damping material is added as a backing to the piezoelectric element before finalizing the assembly. The transducer housing is then sealed to prevent the intrusion of liquids.

The transducer housing 4 is threaded at both the top and bottom ends. An incident angle wedge 6 is threadably coupled to the top end of transducer housing 4. The incident angle wedge 6 acts as the mounting plate for attaching the transducer assembly to the rolling carriage 8 of an automated scanner. Carriage 8 is generally depicted in FIG. 1 as being displaceable over a support surface S along a longitudinal axis L which lies parallel to the longitudinal axis of a welded pipe coupling, e.g., circular cylindrical pipes $P_1$ and $P_2$ joined by a circumferential weld W. The support surface S is itself rotatable about the longitudinal axis of the pipe coupling to effect circumferential scanning of the circumferential weld W.

The angle of refraction within a given material is controlled by the ultrasonic transducer's angle of incidence, i.e., the number of degrees by which the path of propagation is tilted relative to an axis normal to the object surface. The angle of incidence is determined in accordance with Snell's Law, which can be expressed mathematically as:

$$\sin a / \sin b = V_1 / V_2$$

where a is the angle of incidence; b is the angle of refraction; and $V_1$ and $V_2$ are the respective wave velocities in the first and second media. Snell's Law describes wave behavior at an interface between two different media. Although originally derived for light rays, Snell's Law equally applies to acoustic sound (including ultrasound) waves and many other types of waves. The law applies even if mode conversion takes place The angle of incidence may be 0°, in which case the angle of refraction within the material being examined is also 0°.

Figure 3:
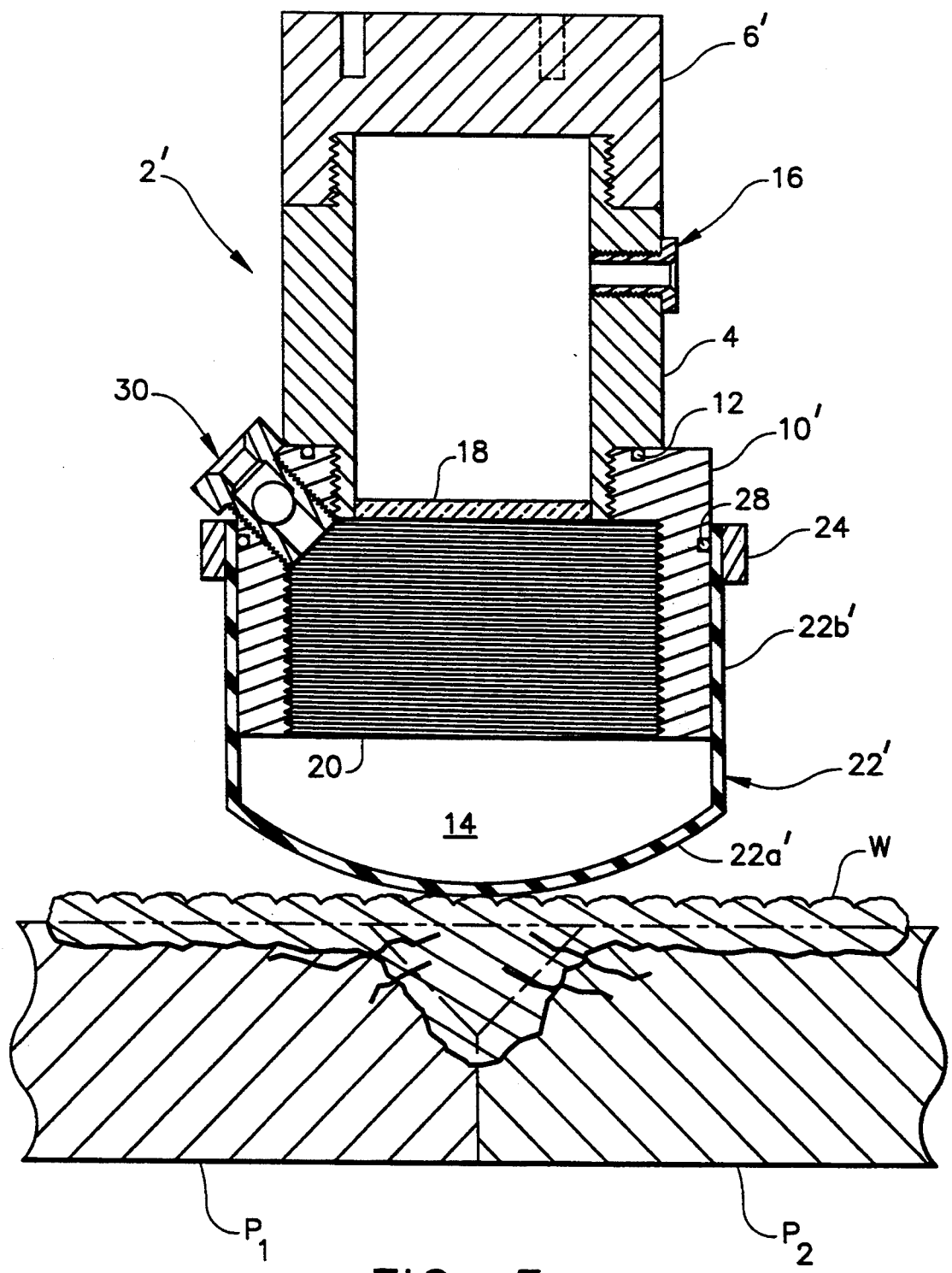
FIG. 3 is a sectional view of a booted ultrasonic transducer in accordance with a second preferred embodiment of the invention, the transducer being shown in contact with but not pressed against the surface of an object to be inspected.

The angles of incidence for the booted transducer in accordance with the invention are dictated by the angle of inclination of the incident angle wedge. FIGS. 1 and 2 depict a transducer in which the angle of inclination of wedge 6, and consequently the angle of incidence of transducer 2, is 10°. In contrast, FIG. 3 shows an alternative preferred embodiment in which the angle of inclination of wedge 6', and consequently the angle of incidence of transducer 2', is 0°. The inclination of the incident angle wedge may be machined to any angle normally associated with ultrasonic testing. The desired angle of incidence depends on the specific liquid couplant used to fill the transducer. The acoustic velocity of the liquid couplant corresponds to $V_1$ of Snell's Law. Therefore if the liquid couplant is water and the desired angle of refraction in mild steel is 43°, then the inclination of the wedge would be machined to an angle of 10°. A 10° angle of incidence will produce both a 43° refracted longitudinal wave beam and a 22.1° refracted shear wave beam.

The angle of inclination is machined into the top surface of the wedge that attaches to carriage 8 of the scanning device. The carriage of the scanning device moves in parallel with respect to the sound beam entry surface of the object being inspected, carrying the transducer across the sound beam entry surface in a controlled raster scanning manner.

Referring again to FIGS. 1 and 2, the threads at the bottom end of transducer housing 4 serve to attach a liquid couplant housing 10 to the transducer. The portion of transducer housing 4 extending between the top and bottom threads has an outer radius which is greater than the outer radii of the threaded portions. The lower edge of the wider transducer housing portion forms a shoulder which abuts the top surface of liquid couplant housing 10. The shoulder serves to compress an O-ring seal 12 arranged in an annular groove formed in the top surface of liquid couplant housing 10 when the transducer housing and liquid couplant housing are tightened together. Seal 12 prevents leakage of liquid couplant through the interface between transducer housing 4 and liquid couplant housing 10.

The liquid couplant housing 10 has first and second threaded bores of different diameter. The first threaded bore of relatively smaller diameter threadably engages the threaded bottom end of transducer housing 4. The second threaded bore of relatively larger diameter forms an ultrasound propagation channel 20. Propagation channel 20 is coated with sound-absorbing material to damp ultrasonic reverberations. The liquid couplant housing is cut at an angle which is the same as or less than the angle of inclination of the incident angle wedge.

The propagation channel 20 is in fluid communication with a liquid couplant-filled chamber 14 formed by an angled transducer boot 22. Channel 20 and chamber 14 are filled with liquid couplant via a valve 30 of the type used on bicycle tires. Valve 30 is coupled to a liquid pump which pumps in the liquid couplant. Any gas trapped inside chamber 14 or channel 20 can form a gap that blocks propagation of the ultrasound through the liquid couplant. To remove gas bubbles or pockets in the couplant, the transducer is tipped so that gases rise into the space immediately proximate to the inlet of valve 30. The valve is then opened to bleed off the gas.

The angled transducer boot 22 is a flexible and wear-resistant membrane made of a molded plastic which is transparent to ultrasound. In the event that the liquid couplant inside chamber 14 and channel 20 is oil, the plastic material must also be resistant to decomposition by oil. The angled transducer boot 22 is molded to have a curved convex contact surface 22a integrally joined on its periphery to a circular cylindrical wall 22b. The longitudinal dimension of wall 22b varies around its circumference.

The circular cylindrical wall 22b has an inner radius slightly greater than the outer radius of liquid couplant housing 10. During assembly, the wall 22b is slid over liquid couplant housing 10 and then clamped thereon using a conventional hose clamp 24 held together by a nut and bolt assembly 26. Alternatively, if the particular application allows the boot to be clamped on with relatively less pressure, a fixed-diameter slip ring made of metal or plastic can be used to clamp the transducer boot onto the liquid couplant housing. The preferred hose clamp is plastic device having opposing toothed jaws which interlock, the teeth being angled to slide over one another and then snap into place as the hose clamp is squeezed onto the transducer using a special hand tool.

An O-ring seal 28 is received in an annular groove machined into the outer circumferential surface of liquid couplant housing 10. The O-ring seal 28 is compressed in the annular groove as clamp 24 is tightened. Seal 28 prevents leakage of liquid couplant through the interface between transducer boot 22 and liquid couplant housing 10.

As shown in FIG. 2, in response to being pressed against the uneven surface of weld W, the convex contact surface 22a flexes inwardly to conform to the contour of the uneven surface to an extent which is dependent on the flexibility of the plastic material. During operation of the ultrasonic transducer, this conformance of the transducer boot 22 to the object surface eliminates air gaps or reduces their size, thereby enhancing the bidirectional ultrasonic coupling between the transducer and the object being inspected.

The ultrasonic transducer shown in FIG. 2 is configured to produce a central ray sound beam of 43° in mild steel. A straight beam configuration in accordance with a second preferred embodiment is shown in FIG. 3. In this case, the central ray sound beam enters the object at a 90° angle of incidence and there is no refraction. The embodiment of FIG. 3 has an incident angle wedge 6' with a wedge angle of 0°, a straight transducer boot 22', and a liquid couplant housing 10' with a wedge angle of 0°. The straight transducer boot 22' is a flexible and wear-resistant membrane made of plastic molded to have a curved convex contact surface 22a' integrally joined on its periphery to a circular cylindrical wall 22b'. The longitudinal dimension of wall 22b' is constant around its circumference. The remaining components are the same as those incorporated in the first preferred embodiment and bear the same reference numerals.

The foregoing apparatus has been disclosed for the purpose of illustration. Variations and modifications of the disclosed apparatus will be readily apparent to practitioners skilled in the art of ultrasonic detection. For example, the angle of inclination of the incident angle wedge may be selected to produce any desired angle of refraction, including but not limited to the exemplary 43° angle described above. All such variations and modifications are intended to be encompassed by the claims set forth hereinafter.

I claim:
1. An ultrasonic transducer comprising:
    a piezoelectric element;
    a transducer housing in which said piezoelectric element is mounted, said transducer housing having a first threaded circular cylindrical surface at one end;
    a support wedge for supporting said transducer housing so that said piezoelectric element is disposed at a predetermined angle of inclination relative to a reference plane, said wedge having a threaded circular cylindrical surface which engages said first threaded circular cylindrical surface of said transducer housing, whereby said wedge and said transducer housing are connected;
    a liquid couplant housing having a channel with first and second open ends and being connected to said transducer housing at an end opposite to said support wedge so that ultrasound waves transmitted by said piezoelectric element propagate through said channel;
    a flexible membrane which is transparent to the ultrasound waves transmitted by said piezoelectric element, said flexible membrane having a first portion which is attached to said liquid couplant housing and a second portion which, in combination with said liquid couplant housing and said piezoelectric element, forms a cavity; and
    a volume of liquid medium which fills said cavity, said liquid medium having the property that ultrasound waves transmitted by said piezoelectric element propagates therein, whereby said flexible membrane is ultrasonically coupled to said piezoelectric element by way of said liquid medium.

2. The ultrasonic transducer as defined in claim 1, wherein said channel of said liquid couplant housing has a threaded circular cylindrical surface.

3. The ultrasonic transducer as defined in claim 2, wherein said threaded circular cylindrical surface of said channel is coated with sound-absorbing material.

4. The ultrasonic transducer as defined in claim 2, wherein said transducer housing has a second threaded circular cylindrical surface and said liquid couplant housing has a threaded circular cylindrical surface which engages said second threaded circular cylindrical surface of said transducer housing, whereby said liquid couplant housing and said transducer housing are connected.

5. The ultrasonic transducer as defined in claim 1, further comprises a rolling carriage to which said support wedge is attached.

6. The ultrasonic transducer as defined in claim 2, wherein said flexible membrane is made of molded plastic having a circular cylindrical portion which surrounds an outer circumferential surface of said liquid couplant housing.

* * * * *